(12) United States Patent
Wade

(10) Patent No.: US 10,568,676 B2
(45) Date of Patent: Feb. 25, 2020

(54) TENSIONING DEVICES AND METHODS FOR DYNAMIC SUTURE SYSTEMS

(71) Applicant: Zimmer, Inc., Warsaw, IN (US)

(72) Inventor: Russell W. Wade, San Clemente, CA (US)

(73) Assignee: Zimmer, Inc., Warsaw, IN (US)

( * ) Notice: Subject to any disclaimer, the term of this patent is extended or adjusted under 35 U.S.C. 154(b) by 91 days.

(21) Appl. No.: 15/787,435

(22) Filed: Oct. 18, 2017

(65) Prior Publication Data

US 2018/0098806 A1    Apr. 12, 2018

Related U.S. Application Data

(63) Continuation of application No. 14/691,573, filed on Apr. 20, 2015, now Pat. No. 9,820,793.

(60) Provisional application No. 61/982,265, filed on Apr. 21, 2014.

(51) Int. Cl.
*A61B 17/88*   (2006.01)
*A61B 17/82*   (2006.01)
*A61B 17/04*   (2006.01)

(52) U.S. Cl.
CPC ...... *A61B 17/8869* (2013.01); *A61B 17/8861* (2013.01); *A61B 17/04* (2013.01); *A61B 17/82* (2013.01); *A61B 2017/0496* (2013.01)

(58) Field of Classification Search
CPC ... A61B 17/8869; A61B 17/82; A61B 17/823; A61B 17/842; A61B 17/8861
See application file for complete search history.

(56) References Cited

U.S. PATENT DOCUMENTS

| | | | |
|---|---|---|---|
| 1,304,620 A | | 5/1919 | Steinkoenig |
| 1,310,232 A | | 7/1919 | Albaum |
| 1,641,077 A | | 8/1927 | Eugene |
| 2,049,361 A | | 7/1936 | Johan |
| 2,291,413 A | | 7/1942 | Siebrandt |
| 2,455,609 A | * | 12/1948 | Scheib ............... A61B 17/8861 140/121 |
| 3,507,270 A | | 4/1970 | Ferrier |
| 4,050,464 A | | 9/1977 | Hall |
| 4,587,963 A | | 5/1986 | Leibinger et al. |
| 4,966,600 A | | 10/1990 | Songer et al. |
| 5,057,113 A | | 10/1991 | Mingozzi |
| 5,116,340 A | | 5/1992 | Songer et al. |
| 5,312,410 A | | 5/1994 | Miller et al. |

(Continued)

OTHER PUBLICATIONS

"U.S. Appl. No. 14/691,573, Non Final Office Action dated Mar. 2, 2016", 17 pgs.

(Continued)

*Primary Examiner* — Julianna N Harvey
(74) *Attorney, Agent, or Firm* — Schwegman Lundberg & Woessner, P.A.

(57) ABSTRACT

A system for repairing separated body tissues includes a tensioning device comprising two proximal handles for grasping, a pair of movable distal tensioning tips, a pivot between the proximal handle and distal tensioning tips, and suture holding clamps proximal to the tensioning tips. The tensioning device is used in conjunction with a buckle with lock bars and a tensioning tab for securing and tensioning suture. The tensioning tab is provided to secure the lock bar in its first position until tension on the suture exceeds a predetermined level.

13 Claims, 9 Drawing Sheets

(56) References Cited

U.S. PATENT DOCUMENTS

| | | | |
|---|---|---|---|
| 5,314,431 A | 5/1994 | Graziano | |
| 5,395,374 A | 3/1995 | Miller et al. | |
| 5,490,856 A | 2/1996 | Person et al. | |
| 5,536,270 A | 7/1996 | Songer et al. | |
| 5,540,698 A | 7/1996 | Preissman | |
| 5,542,843 A | 8/1996 | Price | |
| 5,545,168 A * | 8/1996 | Burke | A61B 17/82 140/106 |
| 5,720,747 A | 2/1998 | Burke | |
| 5,772,663 A | 6/1998 | Whiteside et al. | |
| 5,902,305 A | 5/1999 | Beger et al. | |
| 5,935,133 A | 8/1999 | Wagner et al. | |
| 6,383,200 B1 | 5/2002 | Wotton, III | |
| 6,395,010 B1 | 5/2002 | Wotton, III | |
| 6,443,955 B1 | 9/2002 | Ahrend et al. | |
| 6,752,810 B1 | 6/2004 | Gao et al. | |
| 7,645,284 B2 | 1/2010 | Burbank | |
| 7,871,424 B2 | 1/2011 | Abdelgany | |
| 8,500,739 B2 | 8/2013 | Schoutens et al. | |
| 8,579,901 B1 * | 11/2013 | Foerster | A61B 17/82 606/74 |
| 9,023,058 B2 | 5/2015 | Jaramillo et al. | |
| 9,820,793 B1 | 11/2017 | Wade | |
| 2002/0016593 A1 | 2/2002 | Hearn et al. | |
| 2002/0072753 A1 * | 6/2002 | Cohen | A61B 17/8861 606/103 |
| 2005/0137608 A1 | 6/2005 | Hearn et al. | |
| 2006/0015122 A1 | 1/2006 | Rupp | |
| 2009/0054902 A1 | 2/2009 | Mickiewicz et al. | |
| 2009/0082821 A1 | 3/2009 | Konno et al. | |
| 2010/0042106 A1 | 2/2010 | Bryant et al. | |
| 2011/0112537 A1 | 5/2011 | Bernstein et al. | |
| 2012/0197256 A1 | 8/2012 | Knueppel | |
| 2013/0116736 A1 | 5/2013 | De Oliveira | |
| 2013/0184720 A1 | 7/2013 | Aldridge et al. | |
| 2013/0289564 A1 | 10/2013 | Bernstein et al. | |
| 2014/0142638 A1 | 5/2014 | Goodwin et al. | |
| 2015/0342657 A1 | 12/2015 | Voisard et al. | |

OTHER PUBLICATIONS

"U.S. Appl. No. 14/691,573, Notice of Allowance dated Jul. 19, 2017", 5 pgs.

"U.S. Appl. No. 14/691,573, Response filed Oct. 7, 2016 to Non Final Office Action dated Mar. 2, 2016", 10 pgs.

* cited by examiner

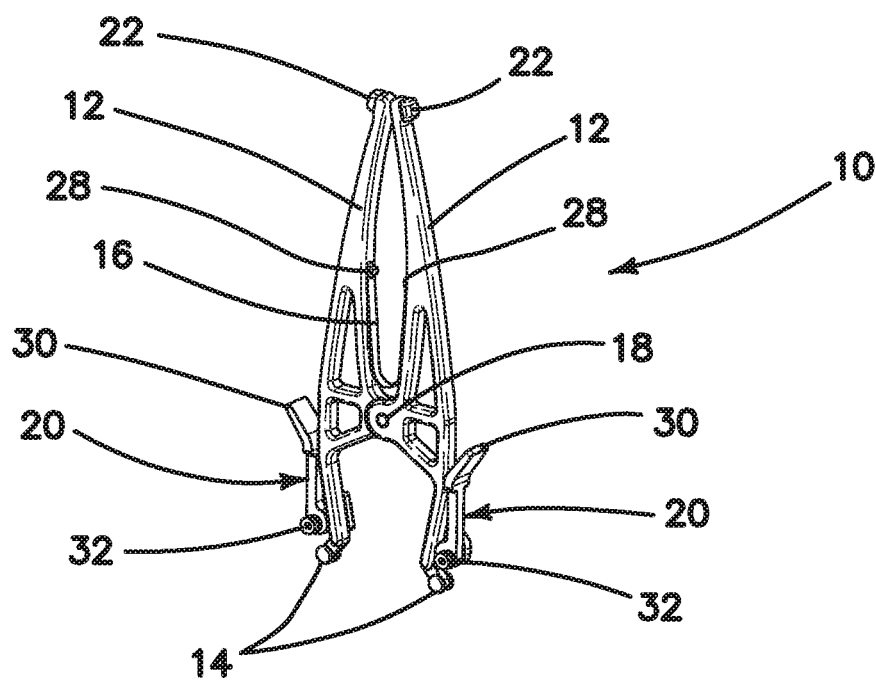
FIG. 6
FIG. 7
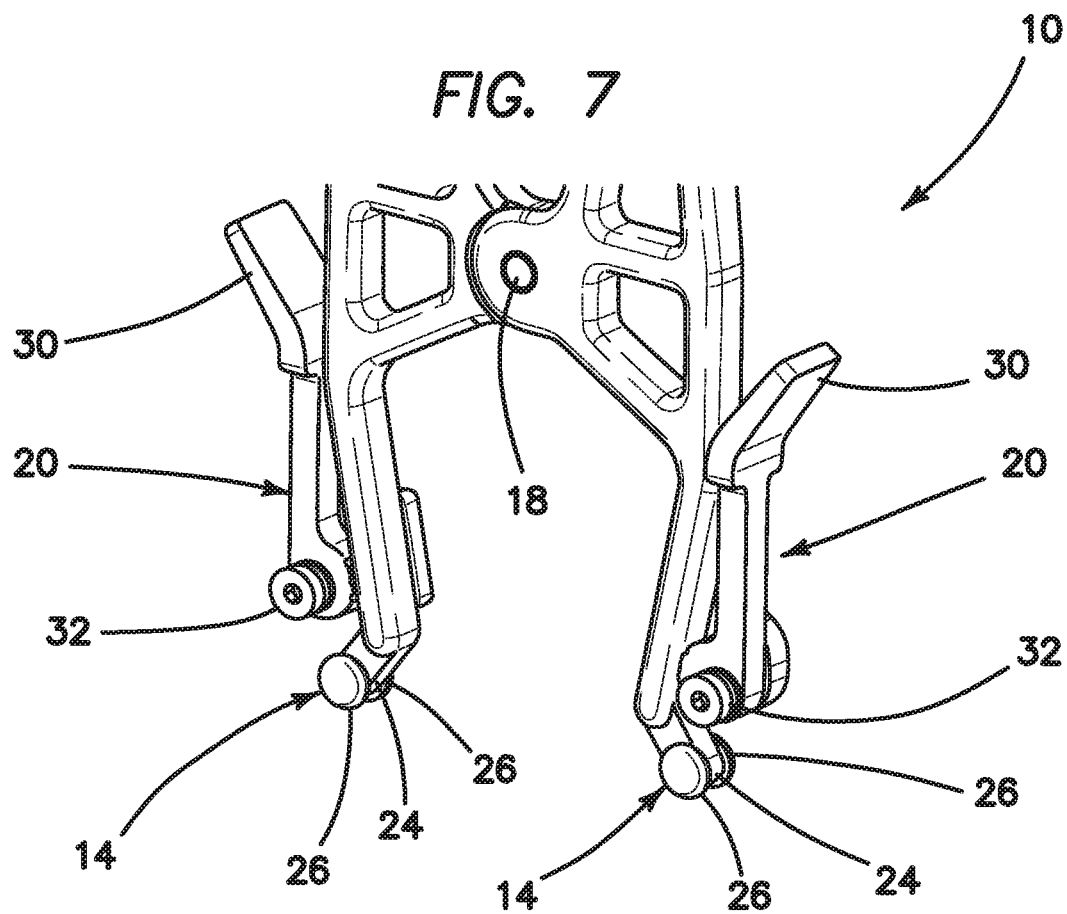

TENSIONING DEVICES AND METHODS FOR DYNAMIC SUTURE SYSTEMS

This application claims the benefit under 35 U.S.C. 119(e) of the filing date of Provisional U.S. Application Ser. No. 61/982,265, entitled Tensioning Device for Dynamic Suture System, filed on Apr. 21, 2014, which application is expressly incorporated herein by reference, in its entirety.

Additionally, this application is related to U.S. Published Patent Application No. 2013/0184720, U.S. Pat. Nos. 8,414, 599, 8,613,755, 8,303,591, U.S. Published Patent Application No. 2014/0018804, U.S. Pat. Nos. 8,579,901, 8,715, 297, 8,668,696, and U.S. Published Patent App. No. 2011/0313435, all of which are commonly assigned and expressly incorporated herein, by reference, in their entirety.

BACKGROUND OF THE MENTION

The present invention is related to the general surgical repair of separated body tissues, and more particularly to internally fixating and stabilizing such body tissues, specifically bones.

In the present state of the art, there are a number of systems available to repair biological tissues separated in surgery or by injury. These products serve to approximate and stabilize the tissues so that healing may commence and provide compression in the interface to promote anatomical heal of tissue. With the correct amount of compression applied to the interface of the tissue portions to be joined, signals are sent to the tissue, thus allowing the tissue to remodel in proper anatomical position. The amount of compression applied to the tissue interface needs to be appropriate to the type of tissue that is being healed.

Twisted wires are typically used to keep bone fragments together so they may heal. Twisted wires only hold tension as long as the twisted wire pair remains stable. Often the wires untwist too soon, thus failing to keep the bone fragments together so that they may heal. Wires can also cut into bone fragments, allowing them to separate so that healing is difficult.

When it is necessary to access the thoracic cavity for a medical procedure, for example, it is required to cut the sternum into two pieces using a sternal saw. Once the procedure is completed within the thoracic cavity, the sternum must be repaired. For such repairs, it is known to use a dynamic compression device. Some of the drawbacks of this typical device, and others which are used include the fact that bulky spring materials used in such devices, while occupying substantial space, often do not store much energy. Some use polymer elastic bands, while others use coiled springs. Additionally, wires are sometimes used to wrap the hones into position in compression with one another. However, wires can have sharp ends that can damage adjunctive tissues. Knot stacks in suture can interfere with the natural movement of surrounding tissues. Another disadvantage of these prior art dynamic compression devices is that current banding systems that incorporate a biasing mechanism to achieve dynamic compression put the biasing mechanism in line with the band or suture. This practice competes with precious space at the healing site. Bands of suture are used to approximate tissues so that they may heal. It is desirable to obtain the best purchase possible on the tissue, so that the binding mechanics offered by the suture may be utilized. The best purchase is optimized by ensuring that the suture has the greatest contact area with the tissue. If a biasing mechanism is interfering with this concept, the biasing mechanism may diminish the suture's ability to hold the tissues together.

In addition, the current banding systems have stiff bands that are not compliant with bony undulations. Flat sutures are used, but are tedious to tie and do not hold reliably.

The banding systems of the present invention are therefore attractive for use in sternal closure because they offer some distinct advantage over twisted wires commonly used in the procedure.

Bands address the issues wires have, as noted in the following discussion. A band, by definition, is wide. In being wide, a band distributes its forces over a wider surface area. This inhibits the band from digging into the bone. In being wide, a band also affords a larger cross-sectional area, whereby more material may be realized, thus presenting the opportunity to offer as much strength in the construct as is necessary to hold the bone fragments together. As such, bands address two main weaknesses of twisted wires. These weaknesses are: digging into the bone fragments being held together, and not having sufficient cross sectional area.

However, with respect to bands, their strength is accompanied by stiffness, as mentioned elsewhere herein. The larger cross-section of the band significantly increases the stiffness of the band. While stiffness and rigidity are good attributes in the sense that they can stabilize the bone union, these attributes can also prevent the band from following the contours of the bone when inserted. This can lead to capturing tissues underneath the band that ultimately destabilize the union as the tissues continue and disappear over time.

Binding the band ends together can also impose some problems. Generally this binding involves a mechanism on the band end that interfaces with holes or slots or contours on the other band end. This creates a tensioning system that is incremental in nature. As in the twisted wire systems, this mechanical interface of the two ends id the weakest link in the banding system. This mechanical interface becomes conductive to fine tuning the tension, so this is problematic. Flat sutures have been used to tie tissues together, but the residual tension supplied in such a knotted structure is insufficient for optimum healing. There is a lot of fuss and time associated with trying to keep and hold a desirable tension with these sutures. What is needed is an attachment means that provides variable tensioning.

Another problem associated with banding systems is that their tension holding capabilities are not sufficient for the environment in which they operate. Tension holding ability can be increased or enhanced by increasing friction at the binding interface of the band. What is needed however is a banding system with the ability to hold tension by selectively increasing friction at the binding interface during locking and/or after locking without increasing friction while tensioning.

What is needed, therefore, are improved devices and techniques for holding two tissue portions in a state of compression and tension that address and overcome these shortcomings in an innovative way.

SUMMARY OF THE INVENTION

The present invention solves the problems outlined above by providing a mechanized tensioning system for consistently and evenly applying a prescribed predetermined level of tension to the suture, at which point the suture is clamped in place with a buckle.

More particularly, there is provided a tensioning device comprising two proximal handles for grasping, a pair of movable distal tensioning tips, a pivot between the proximal handle and distal tensioning tips, and suture holding clamps proximal to the tensioning tips.

The tensioning device is used in conjunction with a buckle that includes a lock bar and tensioning tab for securing and tensioning suture, the tension tab is provided to secure the lock bar in its first position until tension on the suture exceeds a predetermined level.

In one particular aspect of the invention, there is provided a tensioning device for tensioning suture bands having free ends fastenable using a buckle, which comprise a pair of proximal handles for grasping and applying tension, a pair of movable tensioning tips disposed distally to the handles, a spring disposed between the handles for biasing the handles to a desired state, a pivot joining the handles and the tensioning tips so that they are pivotally connected; and suture holding clamps disposed between the tensioning tips and the handles. The combination may also comprise suture guides on a proximal end of each handle for holding and managing excess suture length. The handles for grasping and applying tension are shaped in such a way as to provide mechanical advantage for various hand sizes and holes for lighting device, which also aid in the use of suture clamps. The movable tensioning tips are smooth and round to provide free movement of the band and also include raised sides to prevent band slippage. The spring may preferably comprise a leaf spring and is positioned between the handles with screws in such a way as to provide easy access for cleaning and sufficient force to return handle to original state.

The pivot is positioned in such a way as to provide a desired amount of leverage and travel of the movable tensioning tips, when the handle is squeezed to cause the tensioning tips to move outwardly. The suture holding clamps are disposed between the tensioning tips and the handles and comprise a holder and a toggle clamp. The toggle clamp includes a cam with serrations for gripping suture band and a handle with sufficient length to provide leverage for clamping.

The holder includes a smooth surface for the toggle clamp to rotate on, a feature to stop toggle rotation, and a threaded feature for securing a precision shoulder screw. The suture guides on the proximal ends of the handles-comprise narrow slots with chamfer lead in features to assist in positioning the bands within the narrow slots. The suture holding clamps disposed between the tensioning tips and handles comprise narrow suture holder slots, thumbscrews for clamping, and suture guide pins.

The suture holding clamps disposed between the tensioning tips and handles may comprise suture holder slots, thumbscrews, movable jaws for clamping, and suture guide pins, or may alternatively comprise toggle clamps with dual support toggle clamp holder, and suture guide pins. In yet another embodiment, the suture holding clamps comprise toggle clamps with toggle clamp holder, and suture guide pins.

The tensioning tips comprise pivots, and tensioning leaf springs to control the amount of tension the tensioning device can deliver.

The invention, together with additional features and advantages thereof, may best be understood by reference to the following description taken in conjunction with the accompanying illustrative drawings.

BRIEF DESCRIPTION OF THE DRAWINGS

FIG. 6 is a front isometric view of the tensioning device of FIGS. 1-5 in the open position;

FIG. 7 is a front isometric view of the distal end of the tensioning device of FIGS. 1-6 in the open position;

DETAILED DESCRIPTION OF THE INVENTION

Figure 1:
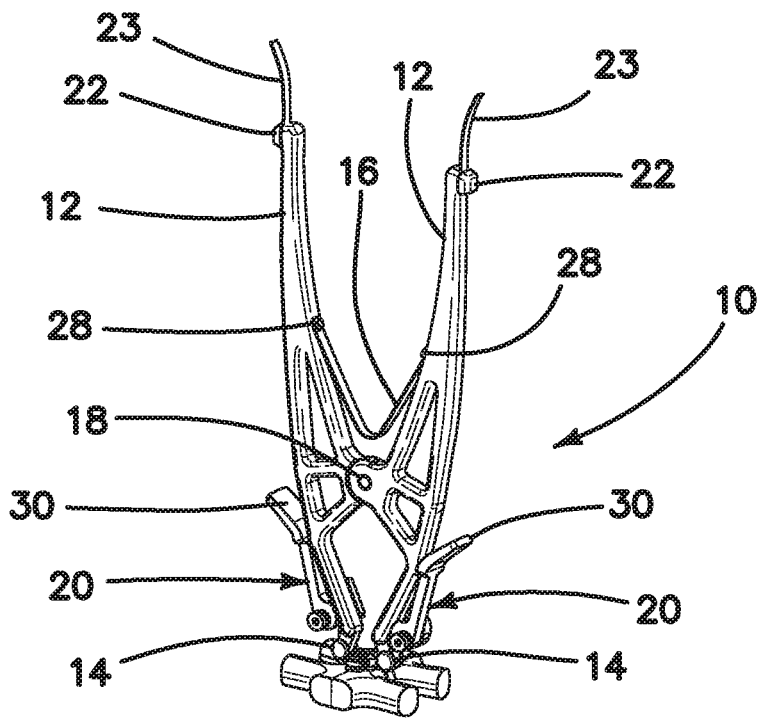
FIG. 1 is a front isometric view of one embodiment of a tensioning device constructed in accordance with the principles of the present invention, including an illustration of a buckle and a band on the sternum.

Referring more particularly to the drawings, there is shown in FIGS. 1-7 a first embodiment of a tensioning system 10 constructed in accordance with the principles of the present invention. The system or device 10 comprises two proximal handles 12, for grasping and applying tension, a pair of movable distal tensioning tips 14 disposed distally to the handles, and a leaf spring 16 disposed between the handles 12 which are biased for returning the handles to their original state. The handles 12 and tensioning tips 14 are pivotally joined together by a pivot pin 18. Suture holding clamps 20 are disposed on the device 10 between the handle portions 12 and the tensioning tips 14, proximal to the tensioning tips, as shown. Suture guides 22 are disposed on the proximal end of handles 12 for holding and managing excess suture length (suture 23). The pivot 18 is positioned in such a way as to provide the right amount of leverage and travel of the movable tension tips 14. When the handles 12 are squeezed, the tensioning tips 14 move outwardly.

Advantageously, the handles 12 are shaped in such a way as to provide mechanical advantage for various hand sizes and include apertures for accommodating a lighting device, which also aid in the use of the suture clamps.

Figure 2:
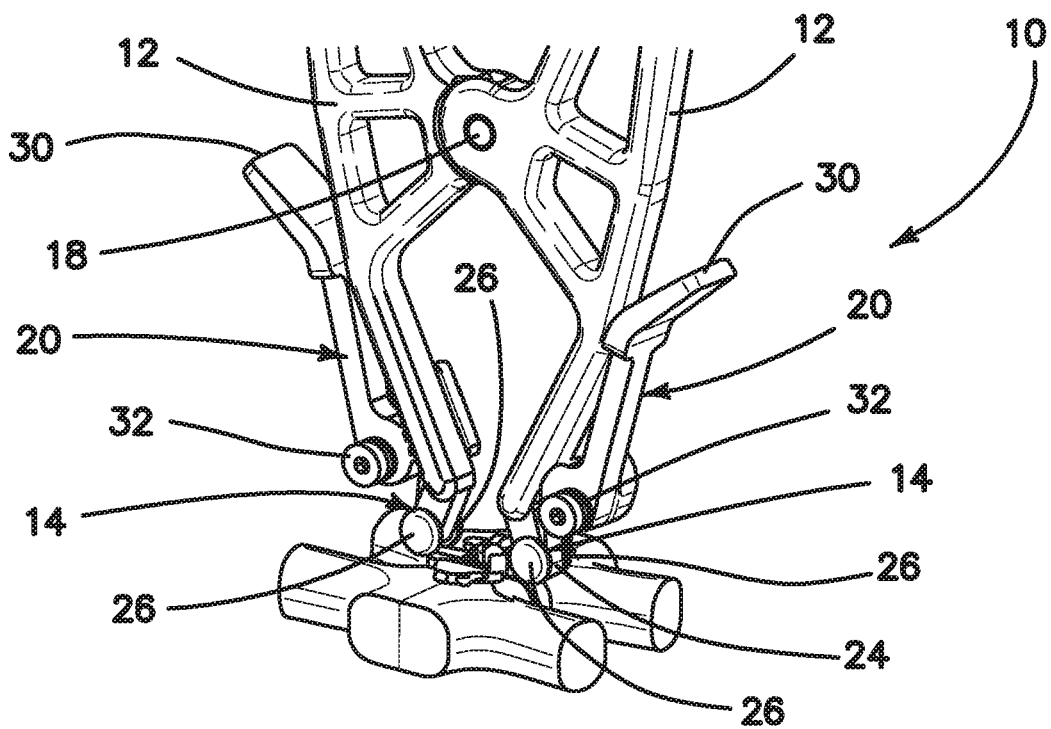
FIG. 2 is a front isometric view of the distal end of the tensioning device of FIG. 1.
Figure 3:
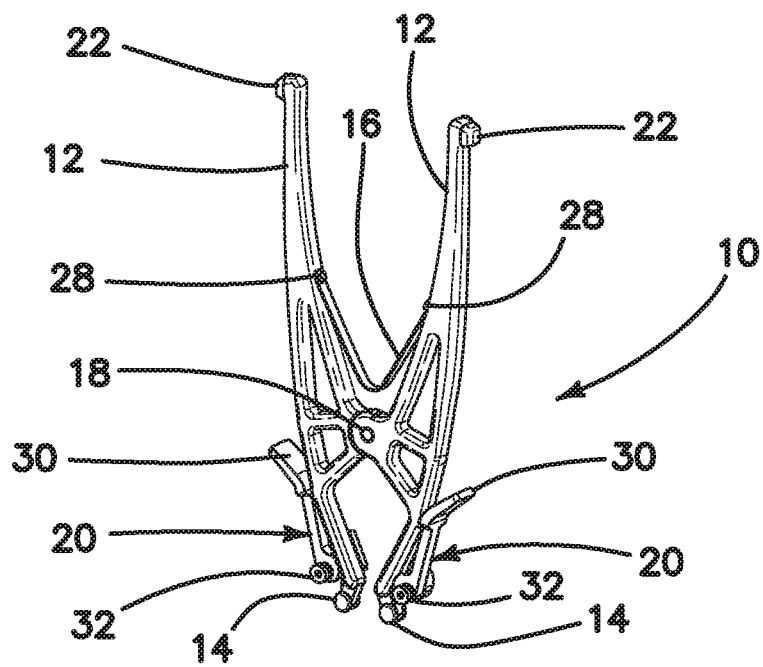
FIG. 3 is a front isometric view of the tensioning device of FIGS. 1 and 2 shown in the closed position.
Figure 4:
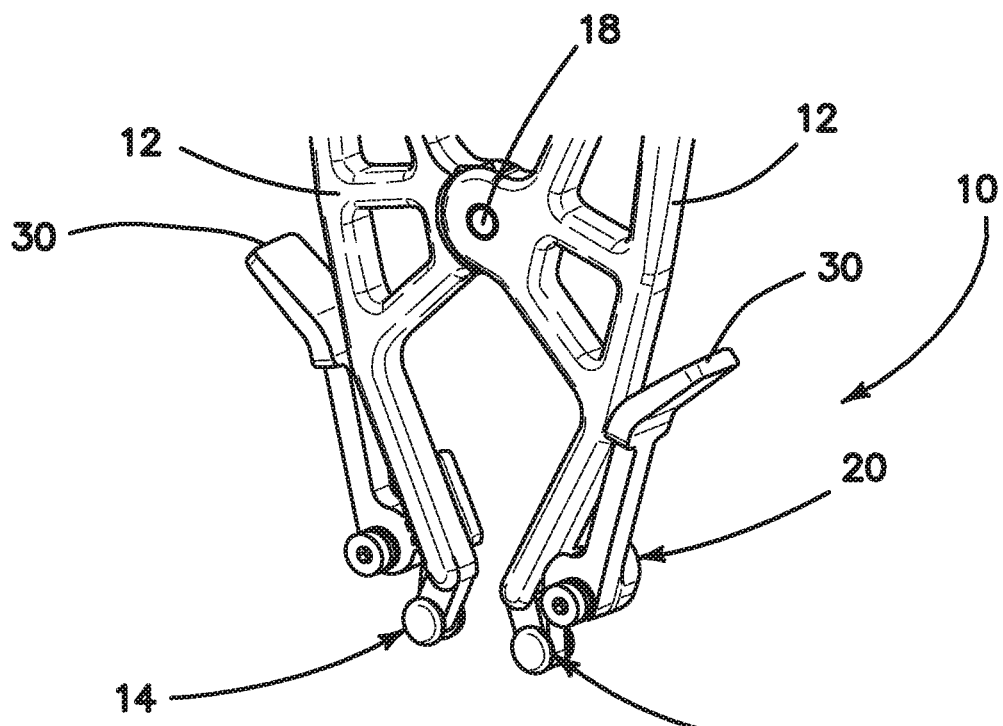
FIG. 4 is a front isometric view of the distal end of tensioning device of FIGS. 1-3 in the closed position.
Figure 5:
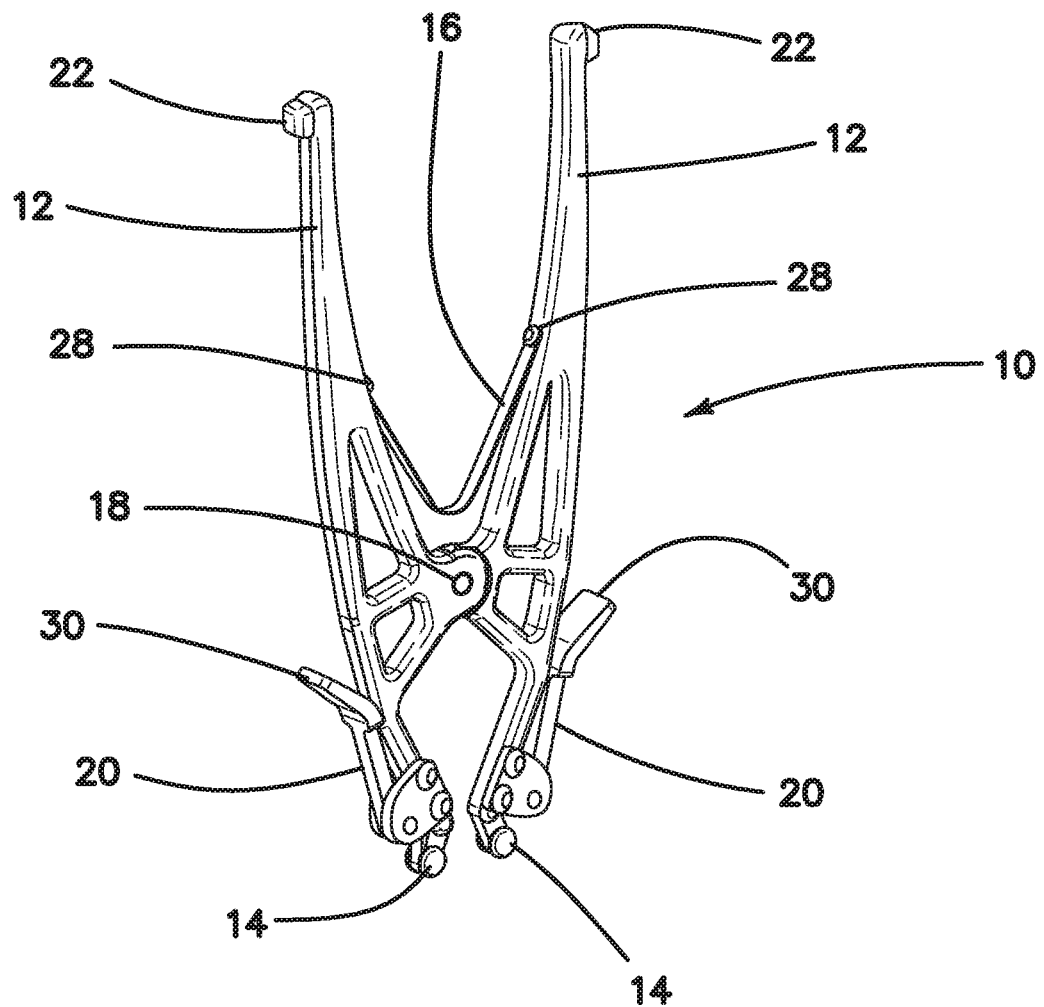
FIG. 5 is a rear isometric view of the tensioning device of FIGS. 1-4 in the closed position.

The movable tensioning tips 14, as illustrated, are round and smooth, for providing free movement of the band. This is best shown in FIGS. 2 and 7. The tips 14 comprise a recessed center portion 24 for accommodating the band, and raised side walls 26 defining the recessed center portion 24 for preventing band slippage.

The leaf spring 16 is positioned between the handles 12, as shown in the drawings, using screws 28, or other suitable fasteners, in order to provide easy access for cleaning and sufficient force to return the handle to its original state.

In the FIGS. 1-7 embodiment, the suture holding clamps 20 include a proximal thumb flange or actuator 30 for pivoting the clamp 20 between open and clamping positions about pivot screws 32.

Figure 8:
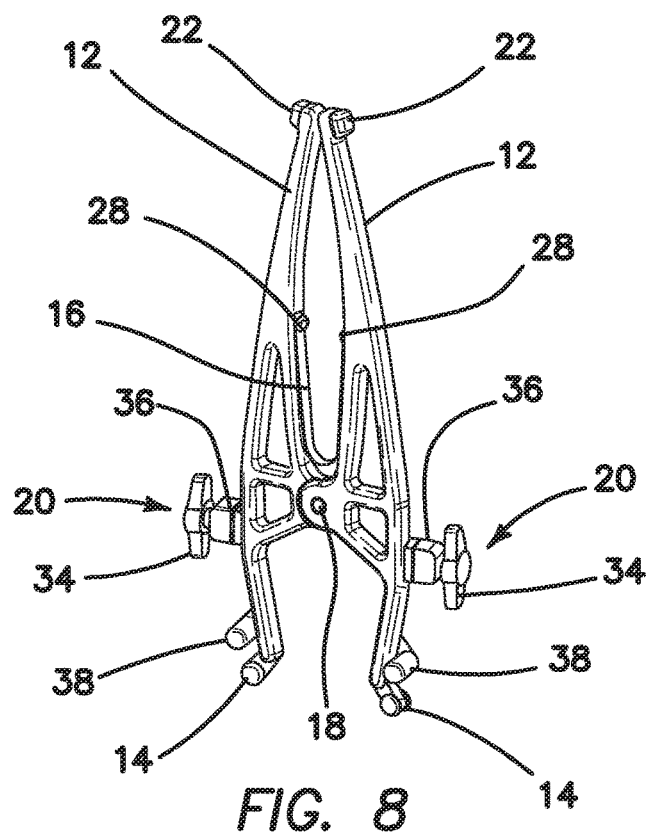
FIG. 8 is a front isometric view of a modified embodiment of the tensioning device of the present invention, using alternate suture holding clamps with thumbscrew, suture guides, and suture guide pins.
Figure 9:
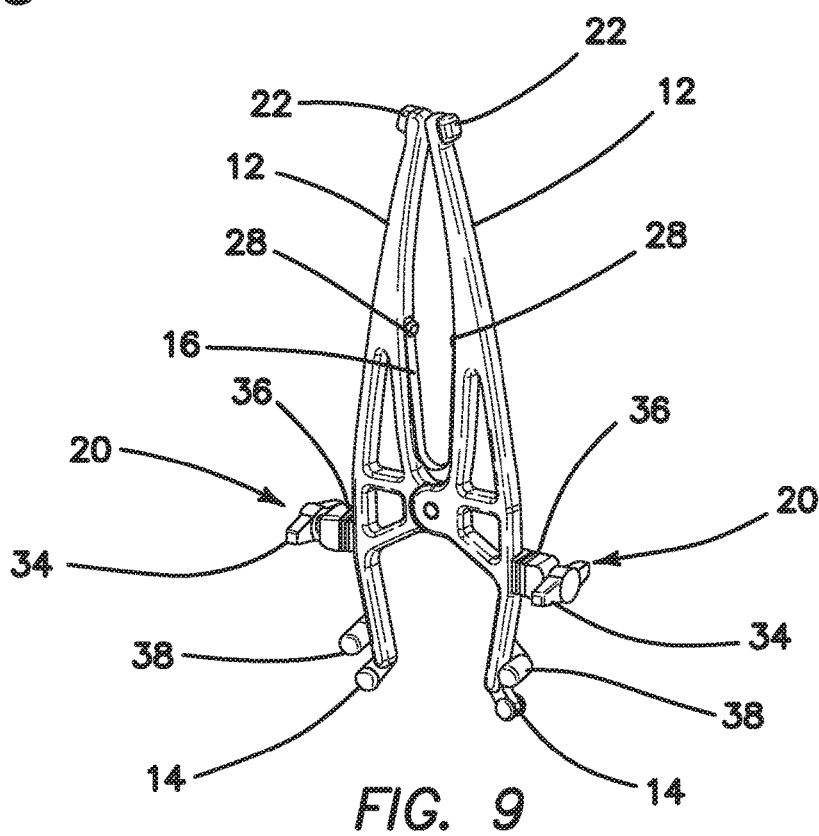
FIG. 9 is a front isometric view of the tensioning device of FIG. 8.

FIGS. 8 and 9 illustrate a modified embodiment of the invention, wherein like elements are identified by like reference numerals to those used in FIGS. 1-7. In this embodiment, however, the suture holding clamp 20 comprises a thumbscrew 34, suture guides 36, and suture guide pins 38.

Figure 10:
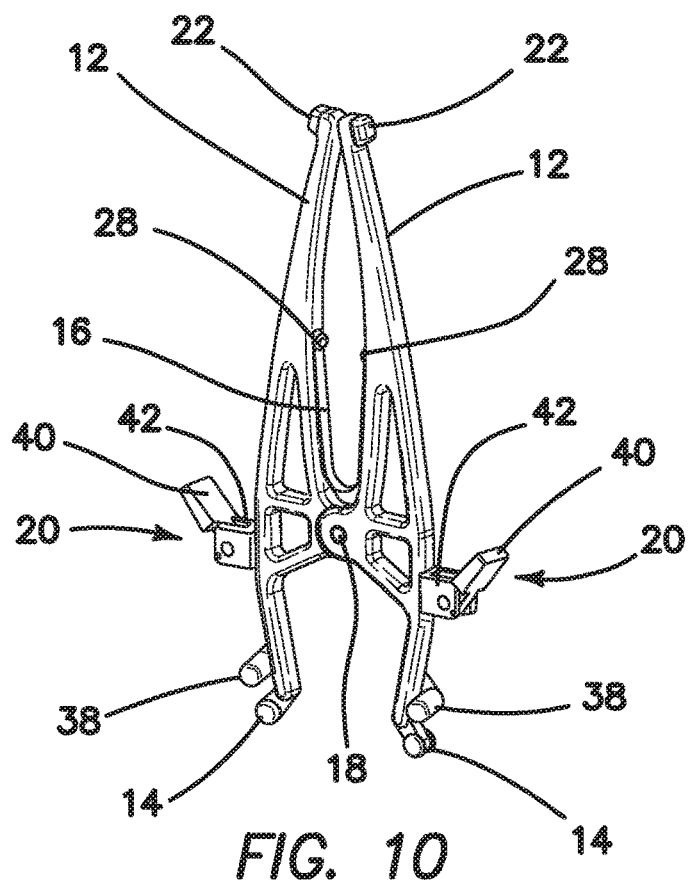
FIG. 10 is a front isometric view of another modified embodiment of the tensioning device of the present invention, using alternate suture holding clamps with toggle clamps, dual support toggle clamp holder, and suture guide pins.
Figure 11:
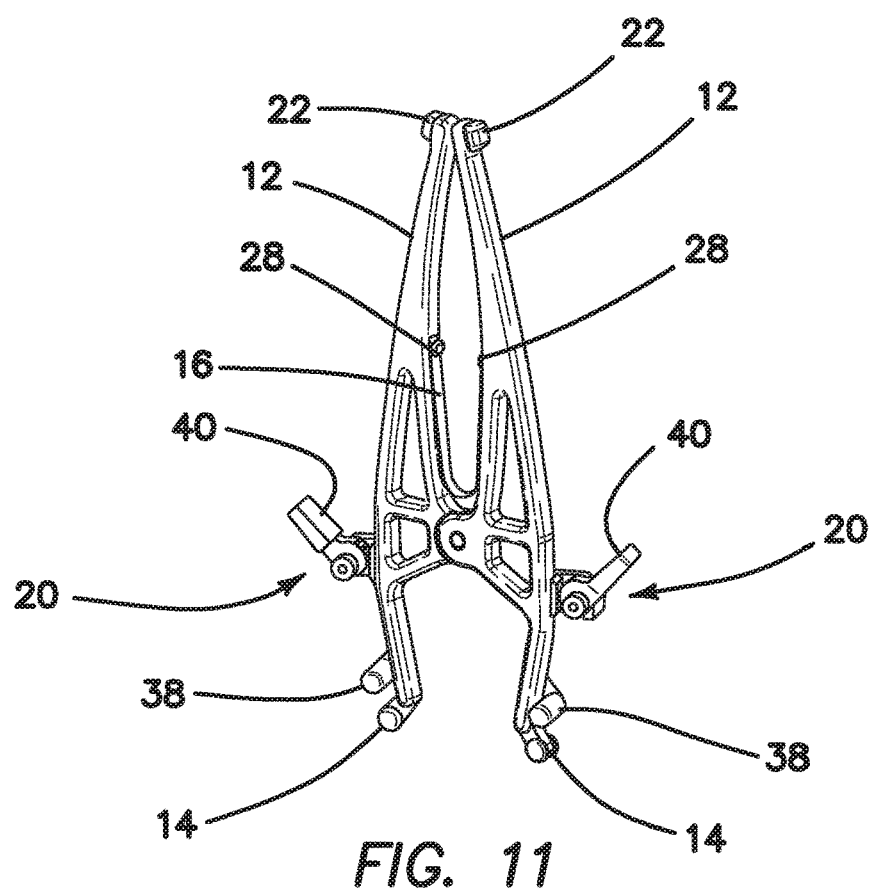
FIG. 11 is a front isometric view of still another modified embodiment of the tensioning device of the present invention, using alternate suture holding clamps with toggle clamps, toggle clamp holder, and suture guide pins.

In FIGS. 10 and 11, two additional modified embodiments are illustrated, wherein, once again, like elements are identified by like reference numerals to those used in FIGS. 1-9. In FIG. 10, the suture holding clamps 20 have been modified, so that they comprise suture guide pins 38, and the clamp 20 comprises a toggle clamp including a toggle actuator 40 for selectively clamping suture within a suture clamping channel 42. FIG. 11 is similar, but includes different constructional details for the suture holding clamps.

Figure 12:
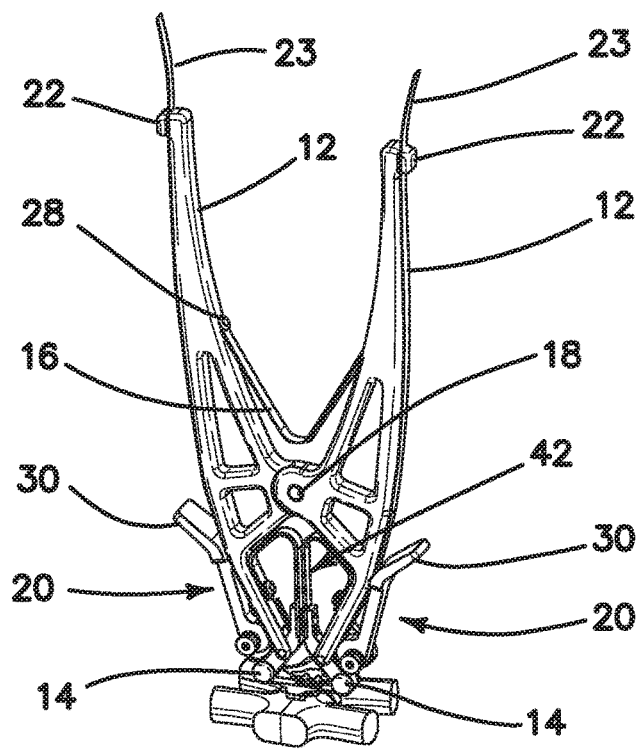
FIG. 12 is a front isometric view of yet another modified embodiment of the tensioning device of the present invention, with pivoting tensioning tips and springs for force control, shown with buckle, band, and no tensioning tab.
Figure 13:
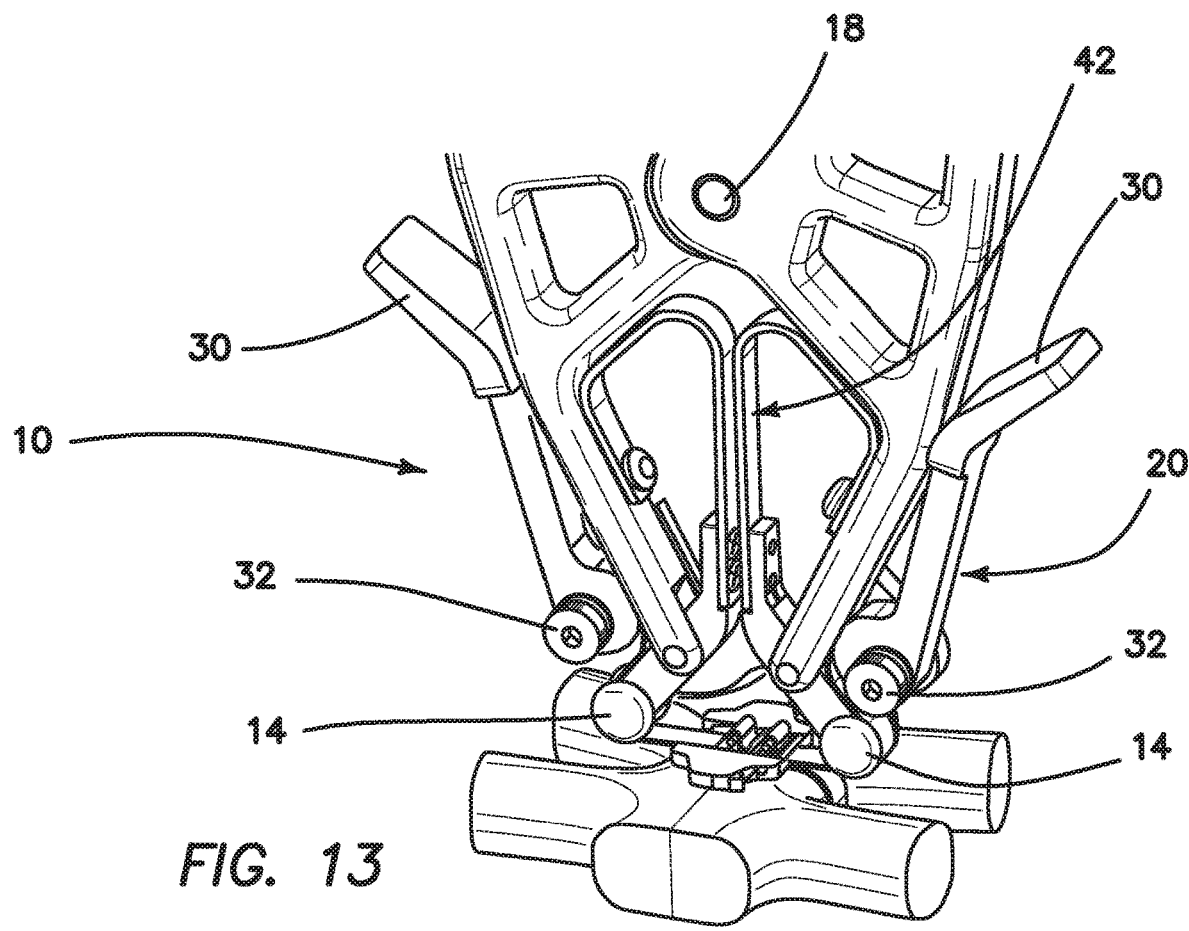
FIG. 13 is a front isometric view of the distal end of the tensioning device of FIG. 12.
Figure 14:
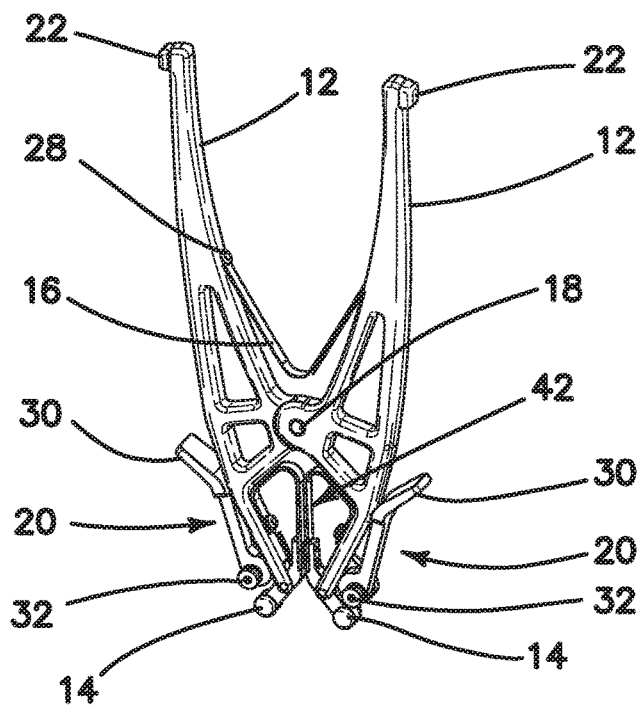
FIG. 14 is a front isometric view of still another modified embodiment of the tensioning device of the present invention, with pivoting tensioning tips and springs for force control.
Figure 15:
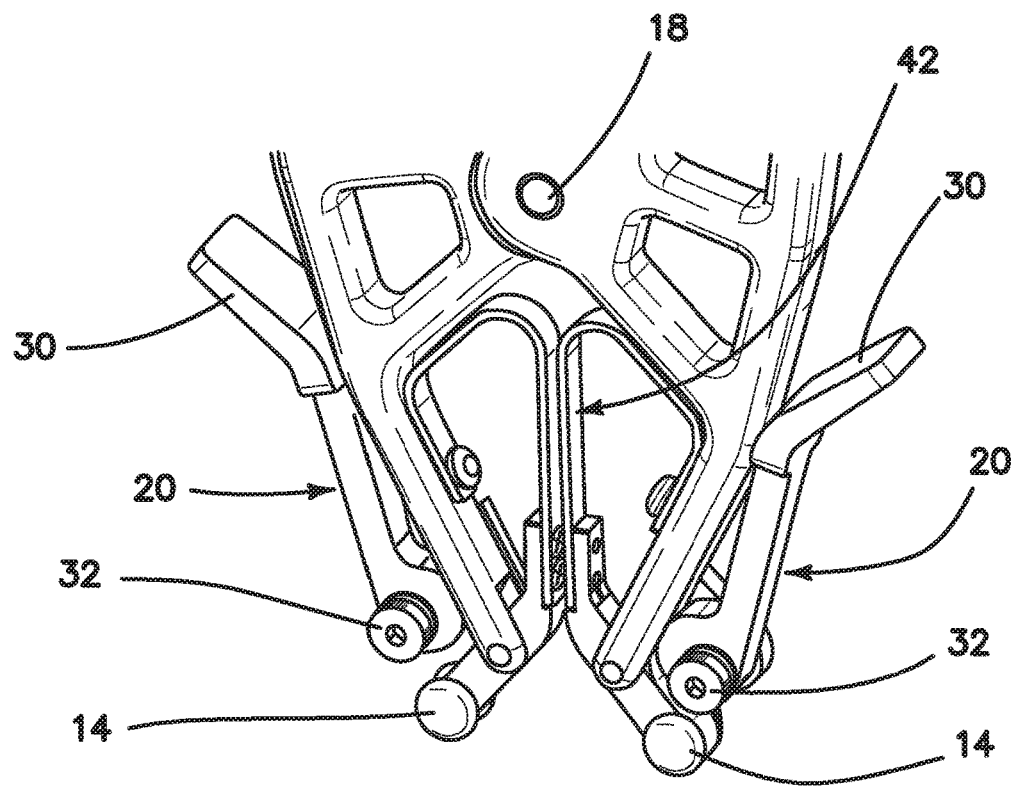
FIG. 15 is a front isometric view of the distal end of the tensioning device of FIG. 14, with pivoting tensioning tips and springs for force control, distal end.

FIG. 12 illustrates yet another modified embodiment of the inventive device 10, wherein, again, like elements are identified by like reference numerals. In this embodiment, a second spring 42 is disposed between the tensioning tips 14 in order to provide force control for the tensioning system. FIG. 13 is an enlarged view of the distal end of FIG. 12. FIGS. 14 and 15 illustrate the FIG. 12-13 embodiment without the sternum and suture buckling system in place.

Figure 16:
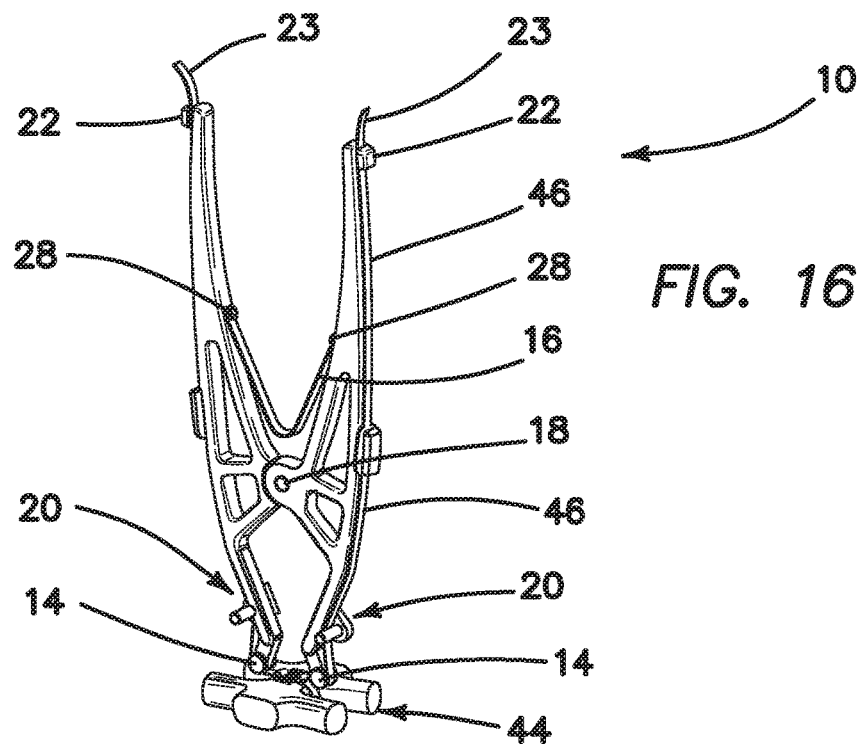
FIG. 16 is a front isometric view of yet another embodiment of the tensioning device of the present invention.
Figure 17:
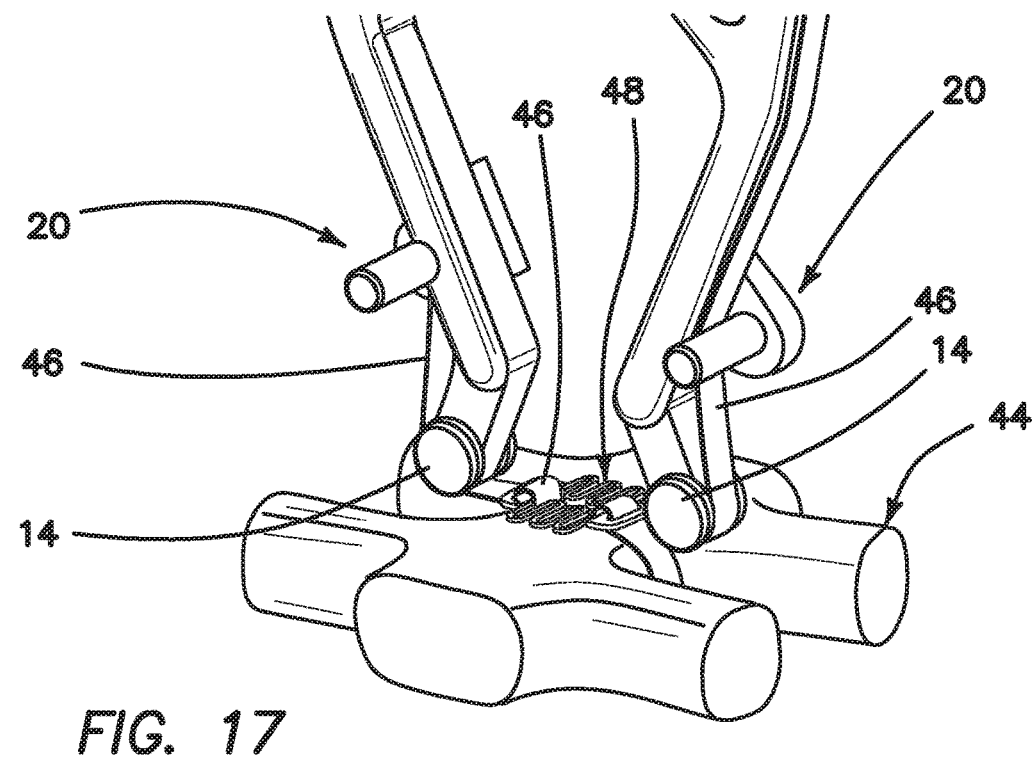
FIG. 17 is a front isometric view of the distal end of the tensioning device of FIG. 16.

FIGS. 16 and 17 illustrate still another modified embodiment of the present inventive device 10. In this embodiment, as in the FIGS. 1-2 and 12-13 embodiments, the embodiment is shown in conjunction with the application for which it has been particularly adapted. That application is in connection with a sternal bone 44 which has been separated for the purpose of performing a surgical procedure, and is now being joined together using a suture band 46, wherein the band is to remain in place about the bone until natural healing takes place. A buckle 48 is utilized to join the free suture ends together, and to adjust the tension on those suture ends. A buckle system of the type shown herein is shown and disclosed in much greater detail in commonly assigned U.S. Published Patent App. No. 2013/0184720, which has already been expressly incorporated herein by reference, in its entirety.

Thus, in practice, the suture band 46 is positioned as desired around the bone 44 to be repaired, and is then tensioned to tighten the band around the bone in order to secure the bone in proper position, and to ensure that the band will remain in tension during the entire healing process, by ensuring that the implant follows the bone as it shrinks during healing. During this tensioning step, a lock bar (not shown) in the buckle remains in an unactuated position, permitting free movement of the suture band 46 through the gap in the buckle 48 as the tensioning proceeds. When a predetermined tensioning force is applied to the suture band 46, the friction forces restraining the lock bar are overcome, and the lock bar breaks free from its restraint, moving to a locking position. This locks the buckle in place, preventing further movement of the suture band 46.

In practice, it is difficult to manage the required amount of force to clamp the suture in place using manual techniques. Thus, the tensioning system shown and described herein assists in applying a consistent and required tension level. As shown, the band 46 passes around each tensioning tip 14, as shown. To retain the suture band in place, it is seated in the tensioning tip recessed center portion 24, between raised side walls 26. The suture bands 46 then extend through the suture holding clamps 20 and along the handles 12 exit the tensioning device through suture guides 22 as suture free ends 23. No threading is necessary. The closed position of the tensioning device 10 occurs when the handles 12 are spaced apart, and the movable tensioning tips are in close proximity (FIGS. 1-5, for example). The open position is shown in 6-9, for example.

When it is desired to apply a tensioning force to the two suture band ends disposed about each of the tensioning tips 14 and over the device 10, the suture holding clamps 20 are actuated to clamp the suture band 46 in place on either side of the device, and the handles are squeezed together to move the device to its open position, with the tensioning tips in their spaced apart orientation. This movement causes tension to be applied to the suture band 46 in the vicinity of the buckle 48. When the suture is tensioned as desired, the buckle is fastened, after which the suture holding clamps 20 can be released, and the handles 12 permitted, by action of the leaf spring 16, to return the tensioner to its relaxed closed position. Then, the suture ends may be trimmed, as desired.

Accordingly, although exemplary embodiments of the invention have been shown and described, it is to be understood that all the terms used herein are descriptive rather than limiting, and that many changes, modifications, and substitutions may be made by one having ordinary skill in the art without departing from the spirit and scope of the invention, which is to be limited only in accordance with the following claims.

What is claimed is:

1. A tensioning system, comprising:
   a suture band;
   a buckle; and
   a tensioning device for tensioning the suture band using the buckle, the tensioning device comprising:
   a pair of proximal handles for grasping and applying tension;
   a pair of movable tensioning tips disposed distally to the handles;
   a spring disposed between the handles for biasing the handles to a desired state;
   a pivot joining the handles and the tensioning tips so that they are pivotally connected; and
   suture holding clamps disposed between the tensioning tips and the handles;
   the tensioning tips movable between an open position and a closed position, wherein the tensioning tips remain spaced apart in the closed position.

2. The tensioning system as recited in claim 1, the tensioning device further comprising suture guides on a proximal end of each handle for holding and managing excess suture length.

3. The tensioning system as recited in claim 1, wherein said handles for grasping and applying tension are shaped in such a way as to provide mechanical advantage for various hand sizes and holes for a lighting device, which also aid in the use of suture clamps.

4. The tensioning system as recited in claim 3, wherein said tensioning tips comprise pivots, and tensioning leaf springs to control the amount of tension the tensioning device can deliver.

5. The tensioning system as recited in claim 1, wherein said movable tensioning tips of the tensioning device are smooth and round to provide free movement of the band and also include raised sides to prevent band slippage.

6. The tensioning system as recited in claim 1, wherein said spring of the tensioning device comprises a leaf spring and is positioned between the handles with screws in such a way as to provide easy access for cleaning and sufficient force to return the handles to an original state.

7. The tensioning system as recited in claim 1, wherein said pivot of the tensioning device is positioned in such a way as to provide a desired amount of leverage and travel of the movable tensioning tips, when the handles are squeezed to cause the tensioning tips to move outwardly.

8. The tensioning system as recited in claim 7, wherein the suture holding clamps disposed between the tensioning tips and handles comprise narrow suture holder slots, thumbscrews for clamping, and suture guide pins.

9. The tensioning system as recited in claim 7, wherein said suture holding clamps disposed between the tensioning tips and handles comprise toggle clamps with dual support toggle clamp holder, and suture guide pins.

10. The tensioning system as recited in claim 6, wherein said suture holding clamps disposed between the tensioning tips and handles comprise toggle clamps with toggle clamp holder, and suture guide pins.

11. The tensioning system as recited in claim 1, wherein said suture holding clamps of the tensioning device are disposed between the tensioning tips and the handles and comprise a holder and a toggle clamp.

12. The tensioning system as recited in claim 6, wherein the suture band comprises first and second free ends.

13. A tensioning system, comprising:
    a suture band;
    a buckle; and
    a tensioning device for tensioning the suture band using the buckle, the tensioning device comprising:
    a pair of proximal handles for grasping and applying tension;
    a pair of movable tensioning tips disposed distally to the handles, the tensioning tips movable between an open position and a closed position, wherein the tensioning tips are spaced closer together in the closed position than the open position;
    a biasing element disposed between the handles for biasing the handles to a desired state;
    a pivot joining the handles and the tensioning tips so that they are pivotally connected; and
    suture holding clamps disposed between the tensioning tips and the handles.

* * * * *

UNITED STATES PATENT AND TRADEMARK OFFICE
CERTIFICATE OF CORRECTION

PATENT NO. : 10,568,676 B2  
APPLICATION NO. : 15/787435  
DATED : February 25, 2020  
INVENTOR(S) : Russell W. Wade Page 1 of 1

It is certified that error appears in the above-identified patent and that said Letters Patent is hereby corrected as shown below:

In Column 8, Line 1, in Claim 10, delete "claim 6," and insert --claim 7,-- therefor In Column 8, Line 9, in Claim 12, delete "claim 6," and insert --claim 1,-- therefor Signed and Sealed this
Twenty-seventh Day of October, 2020

Andrei Iancu
*Director of the United States Patent and Trademark Office*